United States Patent
Kulpakko et al.

(10) Patent No.: US 11,891,649 B2
(45) Date of Patent: Feb. 6, 2024

(54) METHOD FOR DETERMINING LIKELIHOOD OF AN INFLAMMATORY GASTROINTESTINAL TRACT DISEASE

(71) Applicant: Aqsens Health Oy, Turku (FI)

(72) Inventors: Janne Kulpakko, Turku (FI); Anita Jansen, Turku (FI); Riikka Erkkilä, Turku (FI)

(73) Assignee: Aqsens Health Oy, Turku (FI)

( * ) Notice: Subject to any disclaimer, the term of this patent is extended or adjusted under 35 U.S.C. 154(b) by 307 days.

(21) Appl. No.: 17/231,101

(22) Filed: Apr. 15, 2021

(65) Prior Publication Data

US 2021/0348209 A1    Nov. 11, 2021

(30) Foreign Application Priority Data

Apr. 16, 2020   (EP) .................................... 20169854

(51) Int. Cl.
   *C12Q 1/28*      (2006.01)
   *G01N 33/58*     (2006.01)

(52) U.S. Cl.
   CPC ............. *C12Q 1/28* (2013.01); *G01N 33/582* (2013.01); *G01N 2800/065* (2013.01); *G01N 2800/50* (2013.01); *G01N 2800/52* (2013.01); *G01N 2800/7009* (2013.01)

(58) Field of Classification Search
   None
   See application file for complete search history.

(56) References Cited

U.S. PATENT DOCUMENTS

2010/0150842 A1*  6/2010  Ravn ................. G01N 33/5097
                                                      424/9.2

FOREIGN PATENT DOCUMENTS

EP          3299818 A1    3/2018

OTHER PUBLICATIONS

Dotan et al, "Antibodies Against Laminaribioside and Chitobioside are Novel Serologic Markers in Crohn's Disease" Gastroenterology, Elsevier Inc, US, vol. 131, No. 2, XP005587432, ISSN: 0016-5085, DOI: 10.1053/J.Gastro.2006.04.030, Aug. 1, 2006, 13 pages.

European Patent Office, Extended European Search Report, Application No. 20169854.5, dated Aug. 11, 2020, 13 pages.

Gasymov et al: "ANS fluorescence: Potential to augment the identification of the external binding sites of proteins", Biochimica Et Biophysica Acta (BBA)—Proteins & Proteomics, Elsevier, Netherlands, vol. 1774, No. 3, XP005918212, ISSN: 1570-9639, DOI: 10.1016/J.BBAPAP.2007.01.002, Mar. 8, 2007, 9 pages.

Hawe et al, "Extrinsic Fluorescent Dyes as Tools for Protein Characterization" Pharmaceutical Research, Kluwer Academic Publishers-Plenum Publishers, NL, vol. 25, No. 7, DOI: 10.1007/s11095-9516-9,XP019613089, ISSN: 1573-904x, Jan. 3, 2008, 13 pages.

Saha et al, "A sensitive lanthanide label array method for rapid fingerprint analysis of plant polyphenols based on time-resolved luminescence" Analytical Methods, XP55718590, ISSN: 1759-9660, DOI: 10.1039/C9AY01067J, pp. 5044-5054, Jan. 1, 2019, 11 pages.

Seyedian et al, "A review of the diagnosis, prevention, and treatment methods of inflammatory bowel disease", Journal of Medicine and Life, vol. 12, Issue 2, pp. 113-122, XP55718123, DOI: 10.25122/jml-2018-0075, Apr. 1, 2019, Retrieved from the Internet URL: hhttps://www.ncbi.nlm.nih.gov/pmc/articles/PMC6685307/pdf/JMedlife-12-113.pdf.

Vuorinen et al, "Sensitive Label-Free Thermal Stability Assay for Protein Denaturation and Protein-Ligand Interaction Studies", Analytical Chemistry, ISSN: 0003-2700, DOI: 10.1021/acs.analchem.9b05712, XP55718618, Feb. 4, 2020, 5 pages.

* cited by examiner

*Primary Examiner* — Michelle F. Paguio Frising
(74) *Attorney, Agent, or Firm* — Ziegler IP Law Group

(57) ABSTRACT

The aspects of the disclosed embodiments relate to method for determining a likelihood of an inflammatory gastrointestinal tract disease. The method includes diluting a biological sample of a human subject and contacting it with 8-anilinonaphthalene-1-sulfonic acid as modulating agent and further with a reagent, said reagent comprising a peroxidase enzyme and a label selected from a europium chloride and terbium chloride. The sample is incubated and excited, and the time-resolved luminescence signal of the label in the sample is measured. If the luminescence signal is at least 112% higher than for a control sample from a human so subject without of an inflammatory intestine disease, an increased likelihood of an inflammatory intestine disease of the human subject is determined.

11 Claims, 1 Drawing Sheet

METHOD FOR DETERMINING LIKELIHOOD OF AN INFLAMMATORY GASTROINTESTINAL TRACT DISEASE

FIELD

The aspects of the disclosed embodiments relate to a method for determining likelihood of an inflammatory gastrointestinal tract disease from a biological sample of a human subject.

BACKGROUND

Various inflammatory gastrointestinal tract diseases are known, such as irritable bowel syndrome (IBS) comprising Crohn's disease and ulcerative colitis.

These are currently believed to be related to an oxidative stress of the gastrointestinal tract.

IBS is a common condition that affects the digestive system, and causes symptoms like stomach cramps, bloating, diarrhoea and constipation. It is estimated that 45% of people globally are affected by IBS. It is currently diagnosed by measuring the amount of calprotectin in the faeces. This measurement method is however not fast or very reliable, i.e. it can give both false positives and false negatives. For example, in cases when the rectum is frequently emptied, the calprotectin amounts may be normal, while the human subject still suffers from an inflammatory disease within the gastrointestinal tract. Similarly, use of anti-inflammatory drugs may cause false positive results and thus their use should be discontinued for a few weeks before the test.

SUMMARY

The aspects of the disclosed embodiments are directed to a method for an inflammatory gastrointestinal tract disease from a faecal sample of a human subject. It is especially an object to provide a cost-effective, fast and reliable method for these diseases. The aspects of the disclosed embodiments thus relate to a method for determining likelihood of an inflammatory gastrointestinal tract disease, comprising diluting a biological sample of a human subject in an aqueous solution to obtain a diluted sample;

contacting the diluted sample with 8-anilinonaphthalene-1-sulfonic acid as a so modulating agent to obtain a pre-measurement sample;

forming a measurement sample by contacting the pre-measurement sample with a reagent, said reagent comprising a peroxidase enzyme and a label selected from europium chloride and terbium chloride;

incubating the measurement sample;

exciting the measurement sample; and measuring time-resolved luminescence signal of the label in the measurement sample and determining an increased likelihood of an inflammatory intestine disease of the human subject if the luminescence signal is at least 112% higher than for a control sample from a human subject without an inflammatory intestine disease.

The aspects of the disclosed embodiments further relate to a method for evaluating an effect of a treatment of an inflammatory gastrointestinal tract disease, comprising diluting a biological sample of a human subject in an aqueous solution to obtain a diluted sample;

contacting the diluted sample with 8-anilinonaphthalene-1-sulfonic acid as modulating agent to obtain a pre-measurement sample;

forming a measurement sample by contacting the pre-measurement sample with a reagent, said reagent comprising a peroxidase enzyme and a label selected from europium chloride and terbium chloride;

incubating the measurement sample;

exciting the measurement sample; and measuring time-resolved luminescence signal of the label in the measurement sample and comparing the time-resolved luminescence signal of the label in the measurement sample to a time-resolved luminescence signal of the label in a previous measurement sample of the same human subject, in order to monitor the treatment of the inflammatory gastrointestinal tract disease.

The aspects of the disclosed embodiments also relate to a method for evaluating an effect of a treatment of an inflammatory gastrointestinal tract disease, comprising diluting a biological sample of a human subject in an aqueous solution to obtain a diluted sample;

contacting the diluted sample with 8-anilinonaphthalene-1-sulfonic acid to obtain a measurement sample;

incubating the measurement sample; and visually observing the measurement sample and determining an increased likelihood of inefficiency of the treatment of the inflammatory intestine disease of the human subject if an intensification of a colour of the measurement sample is observed.

The aspects of the disclosed embodiments still further relate to a kit of parts comprising a solution of 8-anilinonaphthalene-1-sulfonic acid;

means for taking a biological sample; and means for preparing a measurement sample according to the above method.

The aspects of the disclosed embodiments also relate to use of 8-anilinonaphtalene-1-sulfonic acid in the diagnosis of an inflammatory gastrointestinal tract disease.

DETAILED DESCRIPTION

Figure 1:
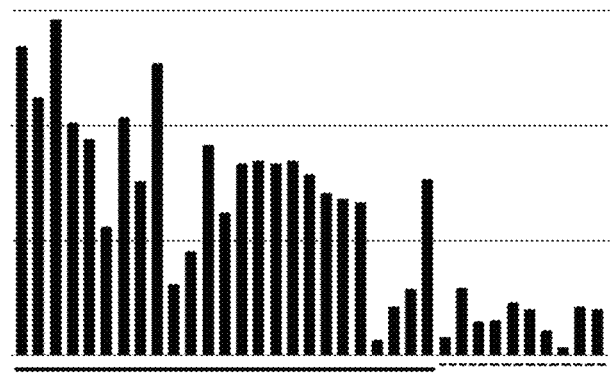
FIG. 1 illustrates results of experiments.

The aspects of the disclosed embodiments thus relate to a method for determining likelihood of an inflammatory gastrointestinal tract disease, comprising diluting a biological sample of a human subject in an aqueous solution to obtain a diluted sample;

contacting the diluted sample with 8-anilinonaphthalene-1-sulfonic acid as a modulating agent to obtain a pre-measurement sample;

forming a measurement sample by contacting the pre-measurement sample with a reagent, said reagent comprising a peroxidase enzyme and a label selected from europium chloride and terbium chloride;

incubating the measurement sample;

exciting the measurement sample; and measuring time-resolved luminescence signal of the label in the measurement sample and determining an increased likelihood of an inflammatory intestine disease of the human subject if the luminescence signal is at least 112% higher than for a control sample from a human subject without an inflammatory intestine disease.

The aspects of the disclosed embodiments provide a cost-effective yet reliable and quick method for screening inflammatory gastrointestinal tract diseases, as is demonstrated below in the Experimental part. Preparation of a sample for the present method takes about 20 minutes, while the test itself takes about 10 minutes. The number of people affected by these diseases is increasing, and the present method can also be used in epidemiological research, in addition to actual screening done in health care. The present method also provides a means for a person suffering from an inflammatory gastrointestinal tract disease to monitor the efficiency of the medication at home.

The aspects of the disclosed embodiments are especially suitable for screening children and young adults (between ages 0 and 25 years), as these diseases typically manifest themselves already in childhood.

In the present method, if the luminescence signal is at least 112% higher than for a control sample from a human subject without of an inflammatory intestine disease, an increased likelihood of an inflammatory intestine disease of the human subject is determined. The luminescence signal can thus be at least 112, 115, 120, 125, 140, 150, 180, 200 or 250% higher than for a control sample, or even higher than this.

It is believed that the aspects of the disclosed embodiments measure the oxidative stress of the gastrointestinal tract, i.e. the superoxide, hypochlorous acid, peroxynitrite and hypochlorite in the biological sample. The compounds are formed in a reaction called oxidative burst (Respiratory burst in human neutrophils, Dahlgren et al., Journal of Immunological Methods, Vol 232, 17.12.1999, p. 3-14).

The compound, called modulating agent, used in the disclosed embodiments, 8-anilinonaphthalene-1-sulfonic acid is very sensitive to these oxygen compounds and in turn modifies the label used. Thus, peroxidase catalyses the oxidation by hydrogen peroxide of 8-anilinonaphthalene-1-sulfonic acid as a modulating agent. This effect has not been observed with catalase enzymes, for example, thus it is believed to be specific to peroxidase enzymes. However, an effect has been observed with N-(2-acetamido)iminodiacetic acid (CAS Number 26239-55-4, from Sigma-Aldrich) as the modulating agent, although its reaction mechanism is believed to be different.

Thus, a clear difference in signals between samples from human subjects suffering from an inflammatory gastrointestinal tract disease and samples from human subjects that do not suffer from such diseases can be seen.

Typically, the present methods do not comprise a step that is practised on a human body.

The label used is europium chloride ($EuCl^{3+}$) label or a terbium chloride ($TbCl^{3+}$) label. These labels exist as complexes, as is known to a person skilled in the art. For example, europium(III) chloride, 99.99%, CAS Number 10025-76-0, from Sigma-Aldrich and terbium(III) chloride, 99.99%, CAS Number 10042-88-3, from Sigma-Aldrich can be used. The europium chloride label can be used for example as a complex of europium chloride, nitrilotriacetic acid (NTA) (for example 99%, CAS Number 139-13-9, from Sigma-Aldrich) and trioctylphosphine oxide (TOPO) (for example 99%, CAS Number 78-50-2, from Sigma-Aldrich). One possible combination is these three components in a 3:9:9 ratio. Instead of NTA, also 2-thenoyltrifluoroacetone (for example 99%, CAS Number 326-91-0, from Sigma-Aldrich) or 4,4,4-trifluoro-1-(2-furyl)-1,3-butanedione (for example 99%, CAS Number 326-90-9, from Sigma-Aldrich can be used.

The concentrations of the various components of a complex of europium chloride 80 nM-5.0 µM for the europium chloride; 5 nM-3 µM for TOPO and; 100 nM-3 µM for NTA. The concentration of europium chloride can thus be for example from 80 nM, 100 nM, 200 nM, 300 nM, 400 nM, 500 nM, 600 nM, 700 nM, 800 nM, 900 nM, 1 µM, 1.5 µM, 2 µM, 2.5 µM, 3 µM, 3.5 µM or 4 µM up to 200 nM, 300 nM, 400 nM, 500 nM, 600 nM, 700 nM, 800 nM, 900 nM, 1 µM, 1.5 µM, 2 µM, 2.5 µM, 3 µM, 3.5 µM, 4 µM, 4.5 µM or 5 µM. The concentration of TOPO can be for example from 5 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 100 nM, 200 nM, 300 nM, 400 nM, 500 nM, 600 nM, 700 nM, 800 nM, 900 nM, 1 µM, 1.5 µM or 2 µM up to 15 nM, 20 nM, 25 nM, 30 nM, 35 nM, 40 nM, 45 nM, 50 nM, 55 nM, 60 nM, 65 nM, 70 nM, 75 nM, 80 nM, 100 nM, 200 nM, 300 nM, 400 nM, 500 nM, 600 nM, 700 nM, 800 nM, 900 nM, 1 µM, 1.5 µM, 2 µM, 2.5 µM or 3 µM. The concentration of NTA can be for example from 100 nM, 200 nM, 300 nM, 400 nM, 500 nM, 600 nM, 700 nM, 800 nM, 900 nM, 1 µM, 1.5 µM or 2 µM up to 200 nM, 300 nM, 400 nM, 500 nM, 600 nM, 700 nM, 800 nM, 900 nM, 1 µM, 1.5 µM, 2 µM, 2.5 µM or 3 µM.

According to yet another embodiment, the peroxidase enzyme is selected from a group consisting of horse radish peroxidase, ascorbate peroxidase, chloride peroxidase, cytochrome c peroxidase, haloperoxidase, lactoperoxidase, myeloperoxidase and mixtures thereof. The test is possible to carry out without the use of peroxidase enzyme (as is done for the simpler test described below), but the results are more difficult to interpret because the reactions are weaker. Thus, it is recommended that for the laboratory test, peroxidase enzyme is used.

According to an embodiment, the label is used in an amount of 4 µl per microtiter well. According to another embodiment, the peroxidase enzyme is used in an amount of 4 µl of 2.5 units per mg diluted in 1 ml of physiological salt solution. One possibility is thus to use the label in an amount of 4 µL of label mixture containing europium chloride 0.717 µM, trioctylphosphine oxide 0.430 µM and nitrilotriacetic acid 0.430 µM (NTA) in dimethyl sulfoxide, and the peroxidase enzyme in an amount of 4 µl of 2.5 units per mg diluted in 1 mL of physiological salt solution.

According to an embodiment, the time-resolved luminescence signal is measured for a time of 200-800 µs after a 200-800 µs delay time. The signal can thus be measured for example for a time of from 200, 250, 300, 350, 400, 450, 500, 550, 600, 650, 700 or 750 µs up to 250, 300, 350, 400, 450, 500, 550, 600, 650, 700, 750 or 800 µs. Independently thereof, the delay time can be for example from 200, 250, 300, 350, 400, 450, 500, 550, 600, 650, 700 or 750 µs up to 250, 300, 350, 400, 450, 500, 550, 600, 650, 700, 750 or 800 µs.

During the preparation of the measurement sample, it is also possible to add a solvent to it before incubation. The solvent may be selected from dimethyl sulfoxide (for example 99.9%, CAS Number 67-68-5, from Sigma-Aldrich), N,N-dimethylformamide anhydrous (for example 99.8%; CAS Number 68-12-2, from Sigma-Aldrich), diisopropyl ether (for example 98.5%, CAS Number 108-20-3) and mixtures thereof.

The inflammatory gastrointestinal track disease which likelihood can be determined with the present method or which treatment efficacy can be monitored with the present method are selected from irritable bowel syndrome (IBS) and inflammatory bowel disease (IBD) comprising Crohn's disease and ulcerative colitis.

According to yet another embodiment, the present method can be used to monitor the treatment of the inflammatory gastrointestinal track disease, i.e. to evaluate the effect of such treatment. This is carried out by measuring samples from a given human subject at different times, for example at time 0 and thereafter every one month, every two months or every six months.

Thus, a method for evaluating an effect of a treatment of an inflammatory gastrointestinal track disease is provided, the method comprising
  diluting a biological sample of a human subject in an aqueous solution to obtain a diluted sample;
  contacting the diluted sample with 8-anilinonaphthalene-1-sulfonic acid as modulating agent to obtain a pre-measurement sample;
  forming a measurement sample by contacting the pre-measurement sample with a reagent, said reagent comprising a peroxidase enzyme and a label selected from europium chloride and terbium chloride;
  incubating the measurement sample;
  exciting the measurement sample; and
  measuring time-resolved luminescence signal of the label in the measurement sample and comparing the time-resolved luminescence signal of the label in the measurement sample to a time-resolved luminescence signal of the label in a previous measurement sample of the same human subject, in order to monitor the treatment of the inflammatory gastrointestinal track disease.

Thus, the method may further comprise comparing the time-resolved luminescence signal of the label in the measurement sample to a time-resolved luminescence signal of the label in a previous measurement sample of the same human subject, in order to monitor the treatment of the inflammatory gastrointestinal tract disease. Generally, at least 40% reduction of luminescence signal compared to first sample is considered as positive treatment response.

In addition to the modulating agent, together with the label, giving clear differences in the time-resolved luminescence signal, the modulating agent is also sensitive to the peroxidase enzyme and reactive oxygen species naturally present in the biological sample (if the human subject is suffering from an inflammatory gastrointestinal track disease), allowing it to be used also alone, for example at home, to give an indication of efficiency of the medication. Indeed, in addition to the time-resolved fluorescence, it is also possible to visually see a change in colour for the sample, which is visible even without the label. The change in colour occurs at wavelengths 456-470 nm. Typically, the intensity of the colour is increased, i.e. the colour becomes deeper. In some cases, the colour can also change from greenish to blue. The change of colour is most typically observed by human eye, but also a colorimeter or a spectrophotometer may be used.

The aspects of the disclosed embodiments thus also relate to a method for evaluating an effect of a treatment of an inflammatory gastrointestinal track disease, comprising
  diluting a biological sample of a human subject in an aqueous solution to obtain a diluted sample;
  contacting the diluted sample with 8-anilinonaphthalene-1-sulfonic acid to obtain a measurement sample;
  incubating the measurement sample; and
  visually observing the measurement sample and determining an increased likelihood of inefficiency of the treatment of the inflammatory intestine disease of the human subject if an intensification of a colour of the measurement sample is observed.

The following embodiments are applicable mutatis mutandis to both methods described above.

Indeed, according to an embodiment, the incubation time is 5-20 minutes. In an especially preferred embodiment, the incubation time is 10 minutes, when the europium chloride label is used.

According to another embodiment, the aqueous solution is a physiological saline solution or tap water or MQ water. Physiological saline solution is preferred, as it is less likely to infer with the measurement results, but clean water can also be used, for example with the home test.

The modulating agent, 8-anilinonaphthalene-1-sulfonic acid is preferably used in an amount of 4 µl of 50 µM solution in the well. The modulating agent can be used in a concentration in a range of 0.2 µM-1000 µM. Thus, the modulating agent may be used in a concentration of from 0.2, 0.5, 1, 5, 10, 15, 20, 25, 30, 35, 40, 45, 50, 55, 60, 65, 70, 75, 80, 85, 90, 95, 100, 120, 150, 200, 250, 300, 350, 400, 450, 500, 550, 600, 650, 700 or 750 µM up to 1, 5, 10, 15, 20, 25, 30, 35, 40, 45, 50, 55, 60, 65, 70, 75, 80, 85, 90, 95, 100, 120, 150, 200, 250, 300, 350, 400, 450, 500, 550, 600, 650, 700, 750, 800, 850, 900, 950 or 1000 µM.

The biological sample is typically selected from a faecal sample, saliva sample, urine sample, blood sample or a bile sample. Naturally, bile samples can only be taken by health care professionals, thus they are more likely to be tested with the method using the label and time-resolved luminescence.

The biological sample is diluted before testing, for example to a dilution that is 5-1000 fold of the original concentration. By 5 fold dilution is meant that there is 1 volume part of sample and 4 volume parts of the aqueous liquid used to dilute the sample for a total of 5 volume parts. The dilution rate can thus be for example from 5, 10, 15, 20, 30, 40, 50, 70, 80, 100, 120, 150, 200, 250, 300, 350, 400, 450, 500, 550, 600, 650, 700, 750 or 800 fold up to 15, 20, 30, 40, 50, 70, 80, 100, 120, 150, 200, 250, 300, 350, 400, 450, 500, 550, 600, 650, 700, 750, 800, 850, 900, 950 or 1000 fold. The dilution depends on the sample. For a method to be used in a commercial scale, the dilution is selected such that the amounts of the other components to be used remain constant, i.e. the test is customised with the dilution rate of the sample. For example, a saliva sample is typically diluted about 10-20 fold, preferably 15 fold, a urine sample about 5-15 fold, preferably 10 fold, a faecal sample about 40-60 fold, preferably 50 fold, a blood sample about 900-1100 fold, preferably 1000 fold and a bile sample about 80-120 fold, preferably 100 fold.

The aspects of the disclosed embodiments still further relate to a kit comprising
  a solution of 8-anilinonaphthalene-1-sulfonic acid;
  means for taking a biological sample; and
  means for preparing a measurement sample according to the above method.

The means for taking a biological sample may comprise for example a sterile plate and a sterile spatula, when the biological sample is a faecal sample. The means for taking a biological sample may be a sterile cup and a sterile syringe, for taking urine samples. Likewise, said means can comprise a sterile needle and a sterile pipette for taking a blood sample or a sterile container and a sterile pipette for taking a saliva sample.

The means for preparing a measurement sample may comprise a sterile cuvette or tube, made from transparent material and having markings showing the user how much of the solvent (for example physiological saline solution or water) is to be added. The solution of 8-anilinonaphthalene-1-sulfonic acid is preferably packaged in a container allowing it to be added dropwise to the cuvette or tube. The kit of parts also comprises use instructions.

The disclosed embodiments still further relate to a kit comprising solution of 8-anilinonaphthalene-1-sulfonic acid and instructions of using it together with a time-resolved luminescence measuring apparatus, i.e. instructions for carrying out the method for determining likelihood of an inflammatory gastrointestinal track disease and/or a method of evaluating an effect of a treatment of an inflammatory gastrointestinal track disease. The kit may also comprise either a database of control samples, an access to such database, or a number of control samples to be used for the comparison. Additionally, the kit may comprise the label.

The disclosed embodiments also relate to use of 8-anilinonaphthalene-1-sulfonic acid in the diagnosis of an inflammatory gastrointestinal tract disease. In other words, the disclosed embodiments relate to a method of using 8-anilinonaphthalene-1-sulfonic acid as a part of the diagnosis of an inflammatory gastrointestinal tract disease. According to a preferred embodiment, the use is ex vivo.

The aspects of the disclosed embodiments can also be defined as a method for determining likelihood of an inflammatory gastrointestinal tract disease, comprising
- diluting a biological sample of a human subject in an aqueous solution to obtain a diluted sample;
- contacting the diluted sample with a modulating agent capable of changing luminescence of a label as the oxidative stress level of the sample changes, to obtain a pre-measurement sample;
- forming a measurement sample by contacting the pre-measurement sample with a reagent, said reagent comprising a peroxidase enzyme and a label selected from europium chloride and terbium chloride;
- incubating the measurement sample;
- exciting the measurement sample; and
- measuring time-resolved luminescence signal of the label in the measurement sample and determining an increased likelihood of an inflammatory intestine disease of the human subject if the luminescence signal is at least 112% higher than for a control sample from a human subject without an inflammatory intestine disease.

Experimental Part

Preliminary experiments were carried out using 35 faeces samples, of which 12 were from human subjects suffering from Crohn's disease, 13 from human subjects suffering from ulcerative colitis and 10 control samples (5 samples from human subjects suffering from childhood rheumatism and 5 from healthy subjects).

Based on the preliminary experiments, faeces samples from 100 arbitrary persons were tested and the luminescence data was compared to calprotectin values measured for the same persons. Thereafter, the results were verified by Valtion Teknillinen Tutkimuskeskus (VTT)

In the following, the term "MQ water" stands for Milli-Q water, which is water that has been purified using an ion exchange cartridge.

The peroxidase used was horse radish peroxidase from Sigma, CAS number 9003-99-0. The other components were from Sigma-Aldrich with concentrations as indicated above.

The IBD and non-IBD faecal samples were processed as follows. Human subject faecal samples in approximately 0.3 ml volume were thawed, added to physiological saline solution until a 1.8 ml volume was reached and subsequently vortexed before sonication 5 minutes in 45° C. Prior to further steps, the samples were centrifuged 10 000 rpm for 5 min to remove any excess solid material. The remaining 0.3 ml clear supernatant was dispensed in 15 ml of physiological saline solution.

First 4 µl of modulator solution was added to the microtiter wells. Modulator consisted of 67 mM of 8-anilinonaphthalene-1-sulfonic acid in MQ water. Next, each sample was divided in three parallel samples of 100 µl volume and pipetted to a 96 well plate.

Finally, 4 µl of label mixture containing europium chloride 0.717 µM, trioctylphosphine oxide (TOPO) 0.430 µM and nitrilotriacetic acid 0.430 µM (NTA) in dimethyl sulfoxide (DMSO) was added to each microtiter well.

After 10 minutes of incubation, luminescence emission intensities were measured in a 400 µs window after a 400 µs delay time using a Victor 2 multilabel counter (Wallac, Perkin-Elmer Life and Analytical Sciences).

Control samples in physiological salt solution: 4 µl of lanthanide label admixture, 4 µl of 67 mM of 8-anilinonaphthalene-1-sulfonic acid, 4 µl of $H_2O_2$ (range: 0.00012% to 0.12%), and 4 µl of horse radish peroxidase (0.25 units to 25 units per mg). Total volume of the sample in the well was 116 µl.

Figure 2:
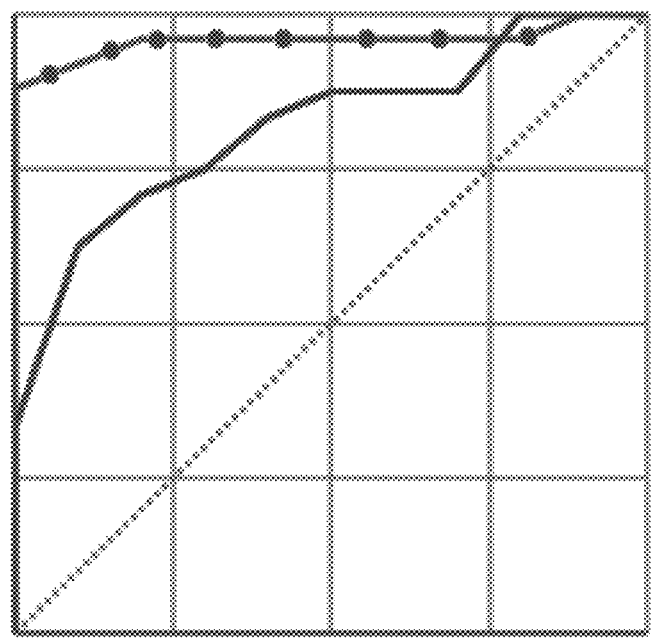
FIG. 2 illustrates further results of experiments.

Results of the luminescence emission intensity measurements are shown in FIG. 1. FIG. 2 shows a ROC comparison graph.

FIG. 1 shows luminescence (on the abscissa) for samples with IBD (i.e. IBD samples, grouped with a continuous line underneath the columns) and for samples without IBD (i.e. non-IBD samples, grouped with a dotted line underneath the columns). The modulator for these results was the 8-anilinonaphthalene-1-sulfonic acid as described above, and the first horizontal line marks a luminescence of 10000, the second horizontal line luminescence of 20000 and the uppermost third horizontal line luminescence of 30000 (the lowest line marking luminescence of 0). As can be seen, the luminescence of the non-IBD samples all remains below 5000 units, while a vast majority of the IBD samples has a luminescence of at least 10000 units. The difference between the results is thus at least 112%.

FIG. 2 is a ROC comparison graph, ROC meaning receiver operating characteristics. On the lower half of the graph, i.e. the right-most rectangle of the graph (as defined by the lower horizontal line, the right-most vertical line and the dashed line) shows the false positive rate and the upper half of the graph, i.e. the left-most rectangle of the graph shows the true positive rate. The line with dots shows the results for samples measured according to the present disclosure and the continuous line without dots illustrates the results for the conventional diagnostic method, using measurement of the amount of calprotectin in the faeces. The graph clearly shows that the present method is more sensitive and more specific, i.e. more reliable and accurate than the state of the art method using calprotectin.

The invention claimed is:

1. A method for determining likelihood of an inflammatory gastrointestinal tract disease, comprising
   - diluting a biological sample of a human subject in an aqueous solution to obtain a diluted sample;
   - contacting the diluted sample with 8-anilinonaphthalene-1-sulfonic acid as modulating agent to obtain a pre-measurement sample;
   - forming a measurement sample by contacting the pre-measurement sample with a reagent, said reagent comprising a peroxidase enzyme and a label selected from europium chloride and terbium chloride;
   - incubating the measurement sample;
   - exciting the measurement sample; and measuring time-resolved luminescence signal of the label in the measurement sample and determining an increased likelihood of an inflammatory intestine disease of the human subject if the luminescence signal is at least 112 percent (-%) higher than for a control sample from a human subject without an inflammatory intestine disease.

2. The method according to claim 1, wherein the time-resolved luminescence signal is measured for a time of 200-8000 µs after a 200-8000 µs delay time.

3. The method according to claim 1, wherein the peroxidase enzyme is selected from a group consisting of horse radish peroxidase, ascorbate peroxidase, chloride peroxidase, cytochrome c peroxidase, haloperoxidase, lactoperoxidase, myeloperoxidase and mixtures thereof.

4. The method according to claim 1, wherein a solvent is added to the measurement sample before incubation, the solvent being selected from dimethyl sulfoxide, N,N-dimethylformamide, diisopropyl ether, and mixtures thereof.

5. The method according to claim 1, wherein the label is used in an amount of 4 µL of label mixture containing europium chloride 0.717 µM, trioctylphosphine oxide 0.430 µM and nitrilotriacetic acid 0.430 µM (NTA) in dimethyl sulfoxide, and the peroxidase enzyme is used in an amount of 4 µl of 2.5 units per mg diluted in 1 mL of physiological salt solution.

6. The method according to claim 1, wherein the label is europium chloride label containing europium chloride, nitrilotriacetic acid and trioctylphosphine oxide.

7. The method according to claim 1, wherein incubation time is 5-20 minutes.

8. The method according to claim 1, wherein 8-anilinonaphthalene-1-sulfonic acid is used in an amount of 4 µL of a solution having a concentration of 10 µM-2000 µM.

9. The method according to claim 1, wherein the biological sample is diluted to a 5-1000 fold dilution.

10. The method according to claim 1, wherein the biological sample is a faecal sample, saliva sample, urine sample, blood sample or a bile sample.

11. The method of claim 1, wherein contacting the diluted sample with 8-anilinonaphthalene-1-sulfonic acid is performed ex vivo.

\* \* \* \* \*